(12) United States Patent
Hocking

(10) Patent No.: US 9,968,774 B1
(45) Date of Patent: *May 15, 2018

(54) METHOD AND SYSTEM FOR CRANIAL SUTURE RELEASE

(71) Applicant: Bruce Hocking, Toronto (CA)

(72) Inventor: Bruce Hocking, Toronto (CA)

(73) Assignee: Center for Pain and Stress Research, Ltd., Toronto (CA)

( * ) Notice: Subject to any disclaimer, the term of this patent is extended or adjusted under 35 U.S.C. 154(b) by 345 days.

This patent is subject to a terminal disclaimer.

(21) Appl. No.: 14/740,956

(22) Filed: Jun. 16, 2015

(51) Int. Cl.
*A61N 1/04* (2006.01)

(52) U.S. Cl.
CPC .................................. *A61N 1/0468* (2013.01)

(58) Field of Classification Search
CPC ........................... A61N 1/0464; A61N 1/0468
USPC .......................................................... 607/115
See application file for complete search history.

(56) References Cited

U.S. PATENT DOCUMENTS

2014/0194949 A1* 7/2014 Wichner ............ A61N 1/36003
607/48

* cited by examiner

*Primary Examiner* — Christopher D Koharski
*Assistant Examiner* — Roland Dinga
(74) *Attorney, Agent, or Firm* — Clifford H. Kraft

(57) ABSTRACT

A method of using of a pair of prior art hand-held device known as the Dolphin Neurostim™ to supply minute, concentrated micro-current impulses to the perimeters of cranial sutures for the purpose of tissue diagnosis (through ohm resistance measurement), promotion pain management (through sympathetic deregulation of the Autonomic Nervous System. The micro-current stimulus (therapy) is delivered through a tiny metallic spring tip (probe) ideally suited for location (detection) of specific treatment points (which have the cellular characteristic of lowered skin resistance). The device concurrently detects, measures, and stimulates therapeutically active treatment points located beside sutures. Once detected, the device is activated to deliver a concentrated (DC) micro-current stimulus through the suture tissue to another identical device located (mirrored) on the opposing side of the suture. This unique stimulation when applied as described in this invention re-balances the autonomic and central nervous systems.

19 Claims, 20 Drawing Sheets

Top view of Application methodology and electrical polarity of devices during Sagittal Suture Release-CRT Method Overview of Application Polarity
during Cranial Release Therapy

Patient Positioning Sagittal Suture Release -SRT Method
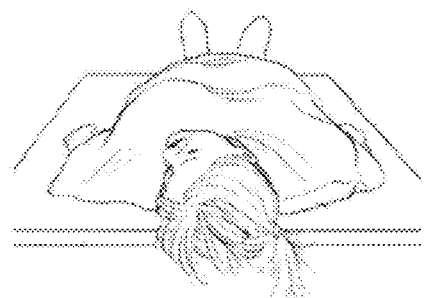
Fig. 2
Anterior view of Application methodology and electrical polarity of devices during Sagittal Suture Release-CRT Method
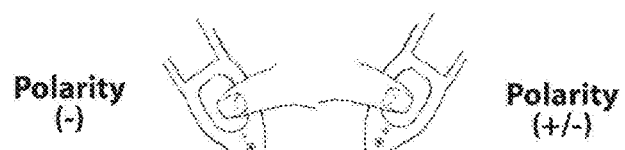
Fig. 3
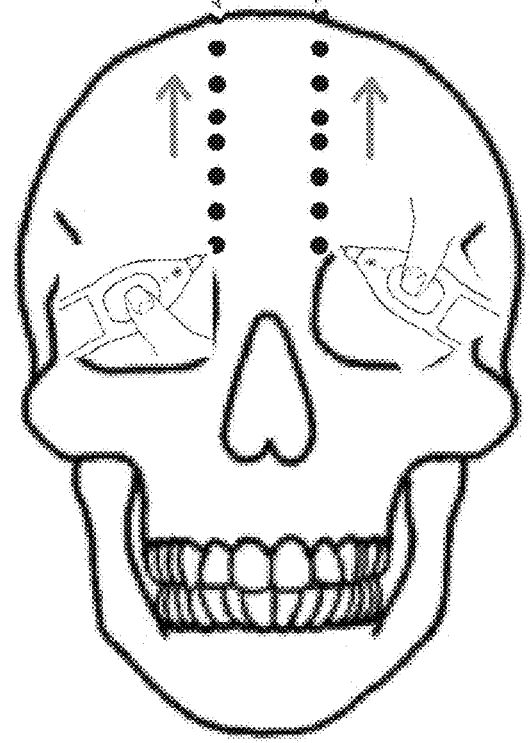

Patient Positioning of
Sphenosquamosal-Coronal
Suture Release-MPS Method
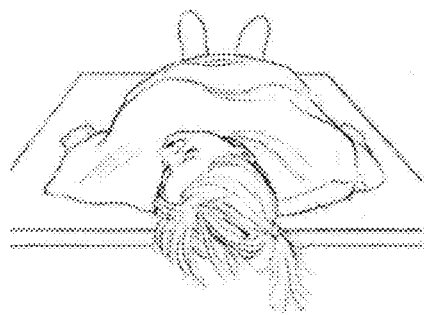
Fig. 6
Application methodology and electrical polarity of devices
during Sphenosquamosal-Coronal
Suture Release-MPS Method
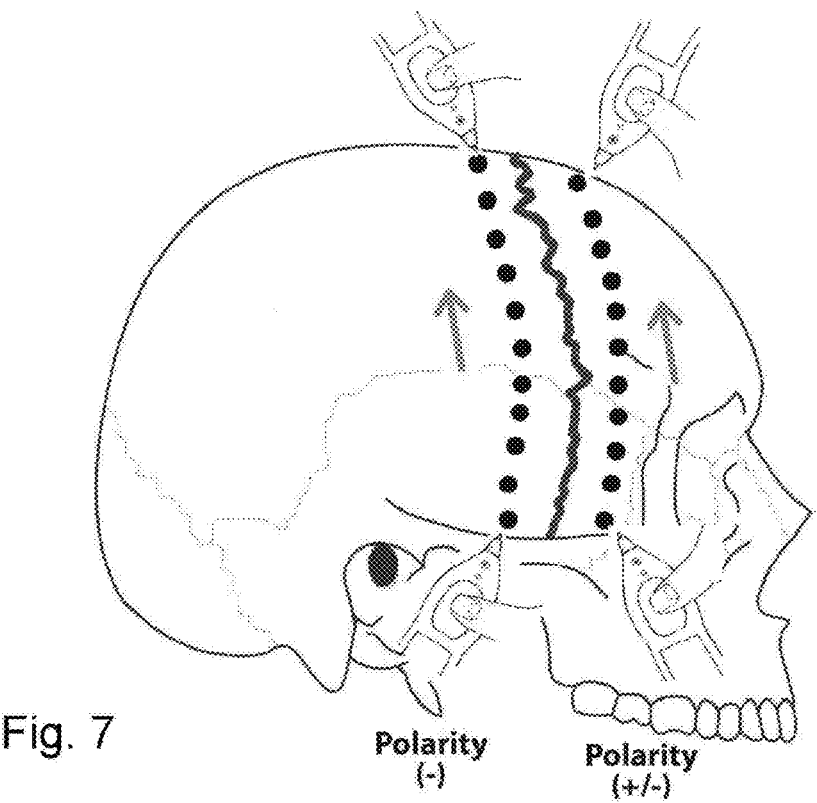
Fig. 7        Polarity        Polarity
              (-)             (+/-)

Patient Positioning Sphenoid-Hip
Balancing -CRT Method

Application methodology and polarity
of Sphenoid-Hip Balancing -CRT Method

GB 27
Polarity
(+/-)

GB 3
Polarity
(-)

**Patient Positioning for Spenofrontal/
Squamosal Suture Release-MPS Method**

**Application methodology and electrical polarity of devices
during Spenofrontal/Squamosal Suture release**

Application methodology and polarity of
Sphenoid-Vagal Tone Release - MPS Method Occipitomastoid-Lambdoid
Suture Release -MPS Method Patient Positioning Application methodology Occipitomastoid-Lambdoid
Suture Release-MPS Method - side View Application methodology Occipitlomastoid-Lambdoid
Suture Release-MPS Method - Posterior View

Application methodology and electrical polarity of devices during increased brain vascularity -CRT Method

Jing Rescue Points B67, Gb 44, Liv 1, Li1, Si1, H9

Application methodology and electrical polarity of devices during increased brain vascularity -CRT Method Gv 20 and Lu 9

Application methodology and electrical polarity
Application methodology and polarity of
Sphenoid-Balance – MPS Method
Gv 16
Polarity
(-)
Taiyang (-)
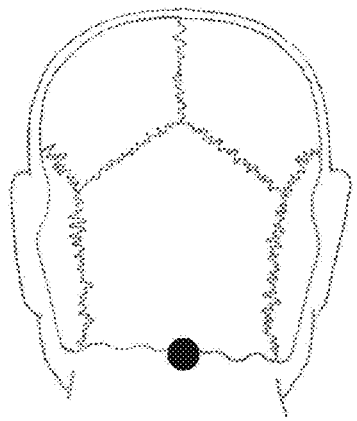
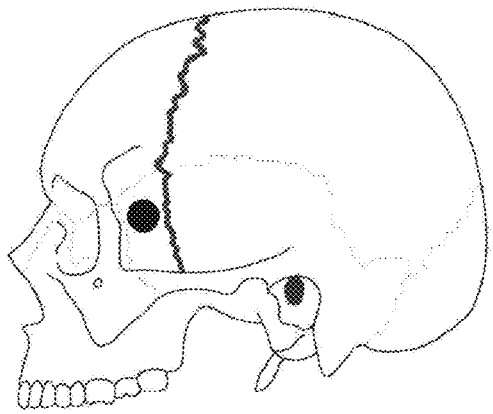
Yintang (-)
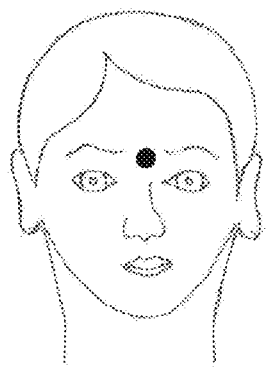
Fig. 22

Application methodology and electrical polarity of devices
during Posterior Neck Release -CRT Method
Gb 20, Gv 16 and Gv 14

METHOD AND SYSTEM FOR CRANIAL SUTURE RELEASE

BACKGROUND

Field of Invention

The present invention relates generally to medical procedures and more particularly to the sequential application of micro-current therapy for the purpose of treatment of cranial sutures for realignment of cranial bones, improved cognitive recovery of post traumatic brain injury and relating imbalances of the nervous system.

Description of the Prior Art

The application of electrotherapy has been an accepted world-wide medical practice throughout the modern history of mankind. Electrotherapy has been applied for the purpose of wound and bone healing, pain and stress management.

Micro-current parameters have been clinically proven to closely approximate the naturally occurring bio-electric currents in the body and therefore more effectively influencing the body's tissue healing and nervous systems. Research has shown that Micro-current enhances three variables critical to healing: ATP (adenosine triphosphate), Protein synthesis, Cellular Membrane transport. Research also shows that only low frequency direct microcurrent can release beta-endorphins, proving a strong influence on the central nervous system.

Concentrated DC micro-current (MPS) appears to provide the strongest enhancement of cellular membrane transport through its unique ability to direct (force) focused micro-current stimulation directly through diseased tissue through as unique application approach. This unique process of simultaneous dual application of negative poled current from one tiny tip through a suture into a second other tip creates a negative poled electrical sewing needle effect throughout the suture which is necessary for localized tissue changes, which in turn produce autonomic nervous system changes.

This novel application approach of MPS quickly changing the cellular bio-electric voltage potentials across sutures, is a key to sympathetic nervous system release. William Garner Sutherland, D.O. (1873-1954) was an American osteopathic physician considered the father of American Osteopathic Medicine. Sutherland was the first osteopathic physician to conceptualize the cranial approach and teach it systematically. Sutherland was the first person to claim to feel a rhythmic shape change in the bones of the cranium, and as he related these movement changes to all body tissues and he saw these movements are the primary agent of influence in dysfunctional tissues.

Cranial osteopathy is now a highly refined and subtle form of manual therapy treatment that encourages balance of the nervous systems through the release of micro-tension between the head bones. It is a gentle yet extremely effective approach and has been used to treat a wide range of conditions for people of all ages, from birth to old age. Osteopaths believe the cranial can negatively influence the body in several manners.

Mechanical Strains:

Midline cranial and facial bones are really an extensions of your spine. If these midline cranial and facial bones are out of alignment they can cause misalignment of the neck, lower back and pelvis. This could cause shoulder, hip and knee problems for instance. Cranial bones are separated by sutures. A suture is a type of fibrous joint which only occurs in the skull, separating head bones. They are bound together by sharpley's fibers, and a tiny amount of movement is permitted at sutures, which contributes to the elasticity of the skull.

These joints are synathrosis, which mean they normally do not move. The bones of the skull remain unfused at birth, and slowly fuse over time, locking up sutures. The relative positions of the bones continue to change during the life of the adult and in old age, cranial sutures may ossify (turn to bone) completely. It is believed by some that the fusion or misalignments of cranial bones is directly linked to the disease and aging process.

These misalignments are quite common and can be caused by things as varied as: Accidents, falls, concussions, birth trauma, whiplash, dental treatment, poor posture, and even emotional trauma. It is well known that mechanical strains through the occiput (the bone that sits on top of your neck) connect mechanically to your spine, twisting in the spinal column and influencing changes. Misalignments of cranial bones cause the sutures physically between them to electrically change polarity which can cause significant adverse changes throughout the body.

Central Nervous System Changes:

When the spine is twisted slightly this can put pressure on the nerves that exit the sides of the spinal column. If this pressure is slight it may cause changes of tone of the muscles supplied by the nerves. This may manifest as pain in certain muscles and joints supplied by those nerves. Pressure on the nerves exiting upper spinal column may cause nerve root irritation throughout entire spine. This can lead to pain, sensation changes or weakness in the arms or legs.

Autonomic Nervous System Changes:

Another possible disruption from misalignment of the cranial bones is to cause imbalance in the autonomic nervous system (ANS). A twist in your occiput can also negatively influence the calming effects of the vagus nerve. The vagus nerve is part of the parasympathetic nervous system and innervates your digestion. If compressed, digestion becomes sluggish and 'toxic', causing uncomfortable symptoms and disease.

Impaired Cognitive Changes:

It is theorized that the displacement of cranial bones can cause electrical depolarization of cranial sutures during concussion or traumatic brain injuries (TBI's). This can cause negative cognitive changes and significantly impair the healing of head injuries, prolonging relating post-concussion symptoms such as headaches, nausea and decreased coordination.

Extensive clinical trials have demonstrated that concentrated micro-current stimulation applied at a low amplitude, low frequency and square waveform can produce the strongest functional changes throughout localized tissues and the nervous systems. The primary goals of this new technique was to apply negative poled concentrated microcurrent stimulation directly through sutures in order to promote increased metabolism, balance the autonomic nervous system and promote cellular homeostasis. Trials outcomes support this electrical balancing of the patient's nervous system as producing long term and significant functional changes in pain and stress patterns. The cellular electrical rebalancing of sutures tissues and the subsequent reverberations throughout the fascial, skeletal, nervous and endocrine systems is exceptionally powerful and is considered medically significant.

This new approach to cranial suture release is called Cranial Release Therapy-MPS Method (CRT-MPS Method).

SUMMARY OF INVENTION

The present invention relates to the use of a pair of prior art hand-held device known as the Dolphin Neurostim™ manufactured and supplied by Acumed Ltd. of Toronto Canada to supply minute, concentrated micro-current impulses to the (outside) perimeters of cranial sutures for the purpose of tissue diagnosis (through ohm resistance measurement), promotion pain management (through sympathetic deregulation of the Autonomic Nervous System. The micro-current stimulus (therapy) is delivered through a tiny metallic spring tip (probe) ideally suited for location (detection) of specific treatment points (which have the cellular characteristic of lowered skin resistance). The device concurrently detects, measures, and stimulates therapeutically active treatment points located beside sutures. Once detected, the device is activated to deliver a concentrated (DC) micro-current stimulus through the suture tissue to another identical device located (mirrored) on the opposing side of the suture. This unique stimulation when applied as described in this invention re-balances the autonomic and central nervous systems.

The present invention is directed to a device and system of treatment using micro-current point stimulation called CRT-MPS METHOD, and is described as the application of concentrated low-level current bilaterally applied to a sutures circumference for the purpose of pain management and health promotion through sympathetic deregulation. CRT-MPS METHOD can provide safe, immediate cellular change with residual benefits and is within the scope of practice of all therapists who are licensed to apply electrotherapy to patients.

DESCRIPTION OF THE FIGURES

Attention is now directed to several drawings that illustrate features of the present invention.

FIG. 2 Sets forth a view of patient positioning for Cranial Release Therapy-MPS.

FIG. 3 Anterior view of Application methodology and electrical polarity of devices during Sagittal Suture Release-CRT MPS Method.

FIG. 6 Patient Positioning of Sphenosquamosal-Coronal Suture Release-MPS Method.

FIG. 7 Application methodology and electrical polarity of devices during Sphenosquamosal-Coronal Suture Release-MPS Method.

FIG. 22. Application methodology and electrical polarity Application methodology and polarity of Sphenoid-Balance-MPS Method Gv16—Yintang.

Figure 1:
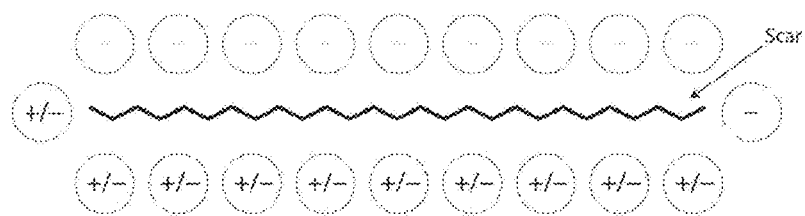
FIG. 1 Sets forth a top overview of electrical polarity of sutures and current during CRT-MPS application.
Figure 4:
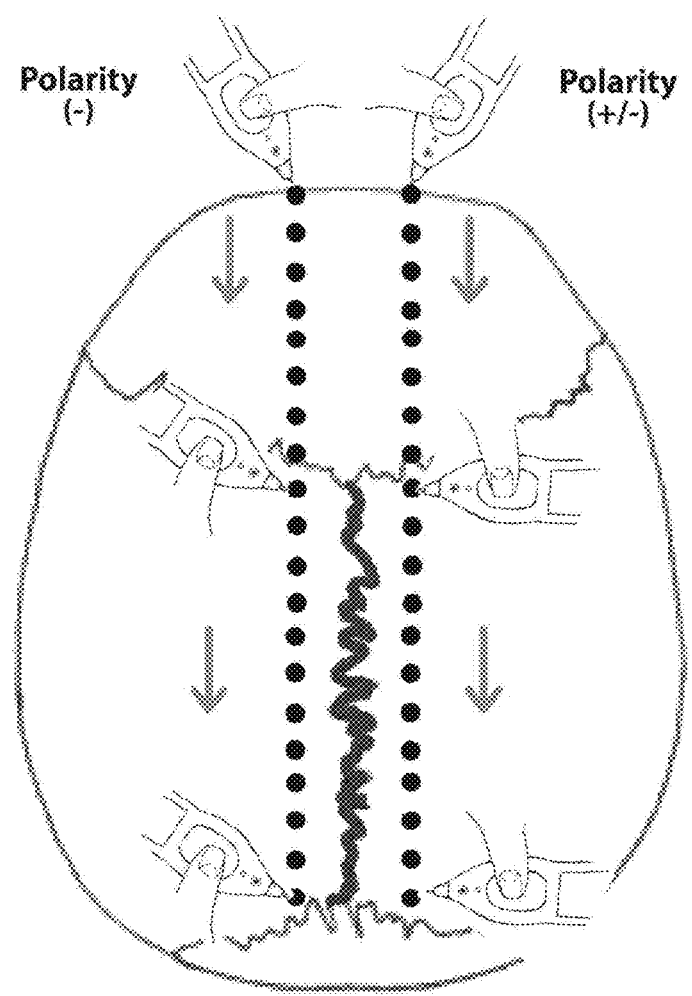
FIG. 4 Top view of Application methodology and electrical polarity of devices during Sagittal Suture Release-CRT MPS Method.
Figure 5:
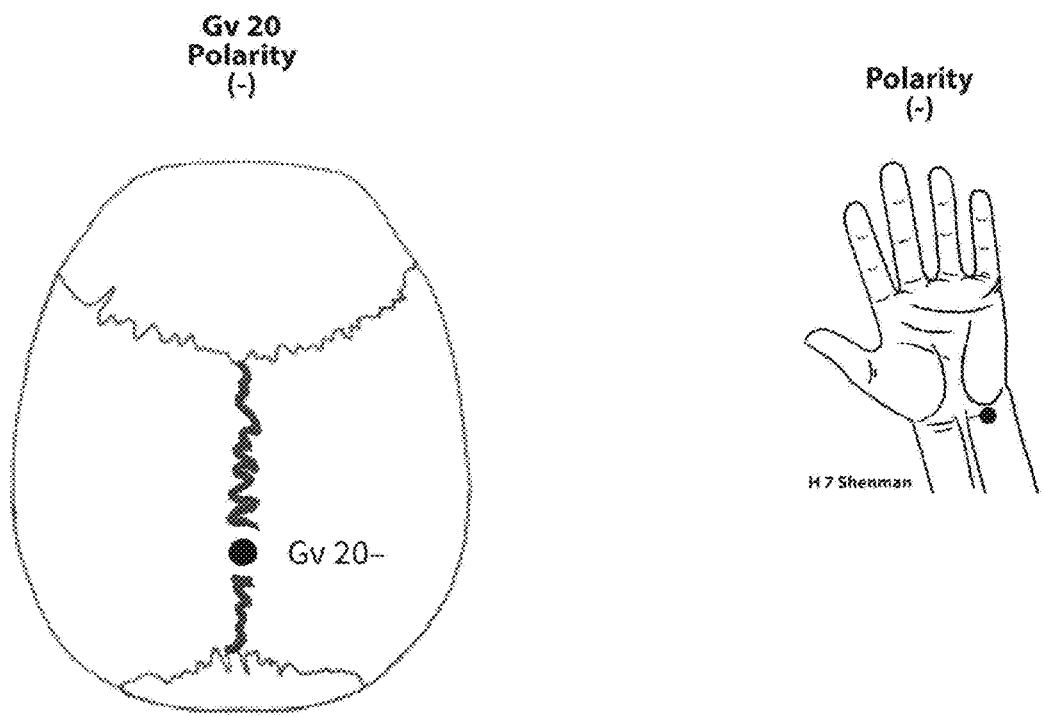
FIG. 5 Application methodology Autonomic Nervous System (ANS) Balancing-CRT MPS Method—Gv20-H7.
Figure 8:
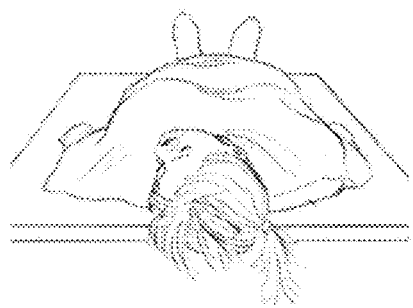
FIG. 8 Patient Positioning Sphenoid-Hip Balancing-CRT MPS Method.
Figure 9:
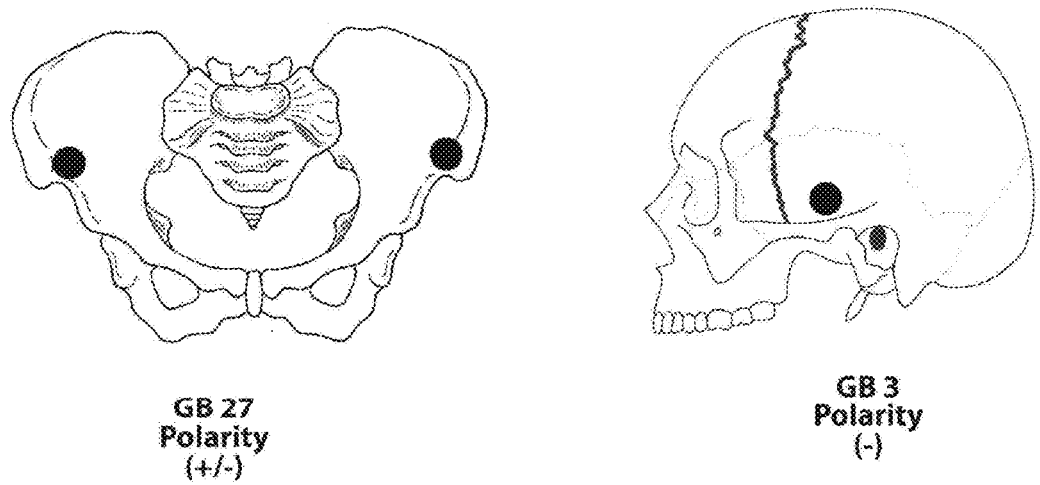
FIG. 9 Application methodology and polarity of Sphenoid-Hip Balancing-CRT MPS Method—Gb27-Gb3.
Figure 10:
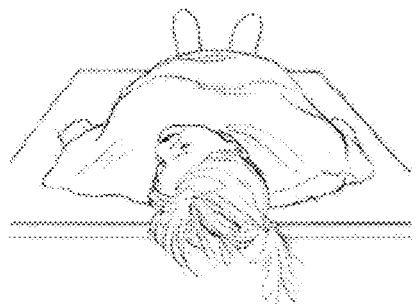
FIG. 10 This figure illustrates a top view of the methodology placement and polarity settings of unit one and unit two during Scar Release Therapy-MPS Method.
Figure 11:
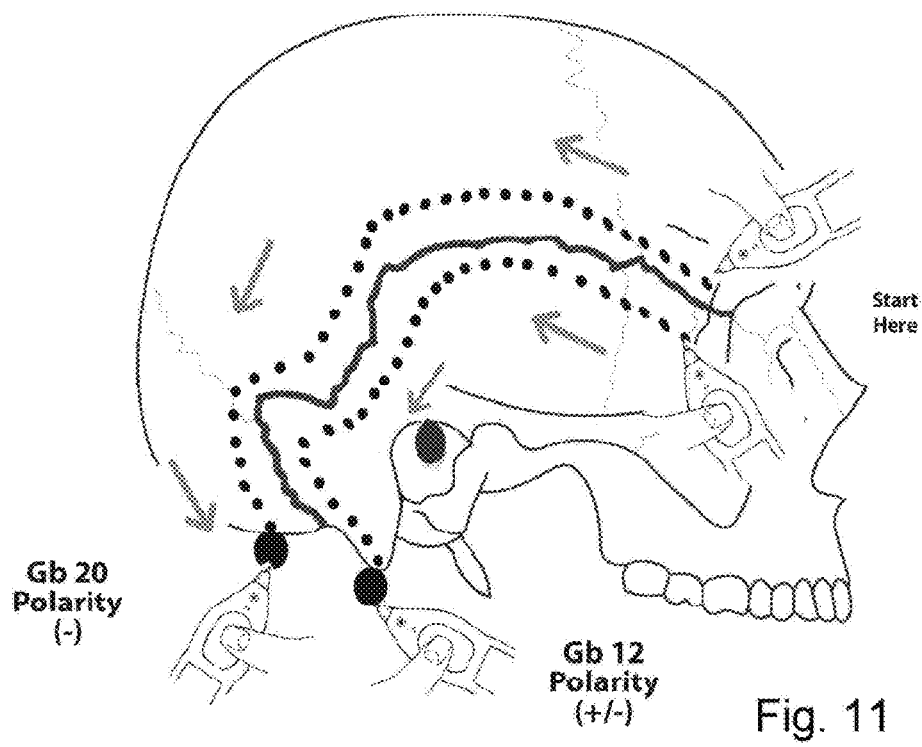
FIG. 11 This figure illustrates a top view of the direction of application methodology and electrical polarity of unit one and unit two devices during SRT-MPS para-scar treatment.
Figure 12:
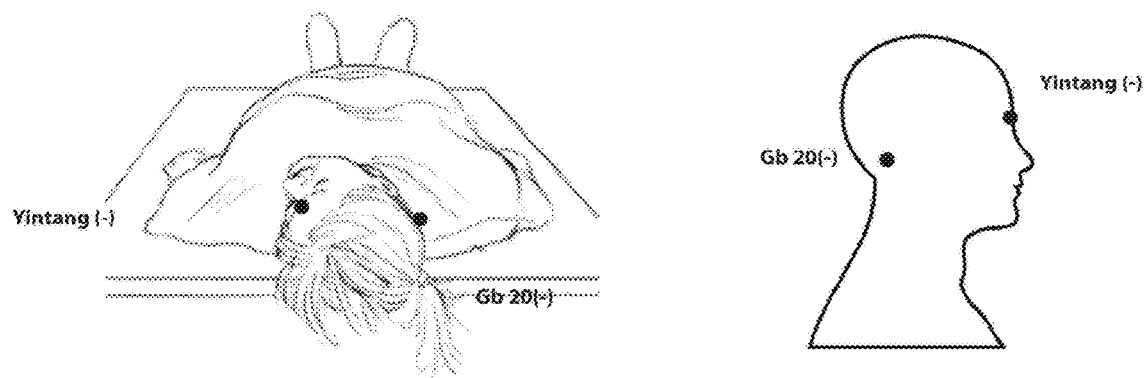
FIG. 12 This figure illustrates a top view of the application methodology and electrical polarity of devices during SRT-MPS opposite end treatment.
Figure 13:
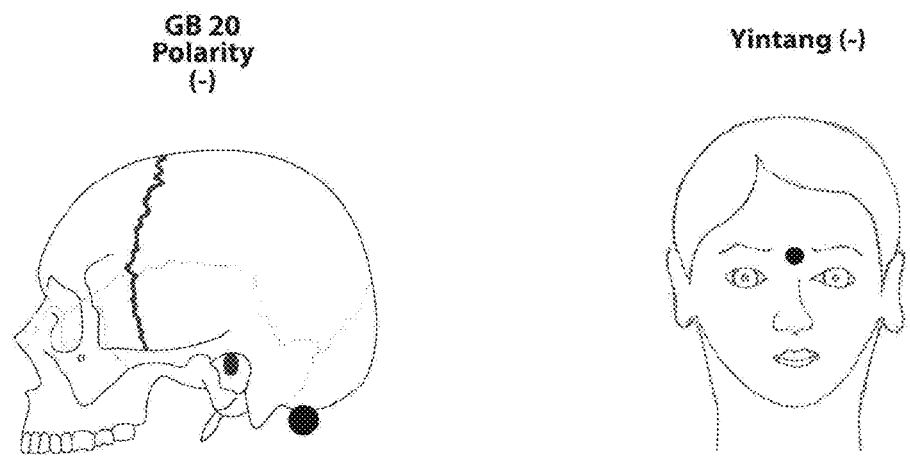
FIG. 13 This figure illustrates a view of acupuncture point B 62 and the methodology placement and polarity settings of unit one and unit two during Fascia Release-SRT Method.
Figure 14:
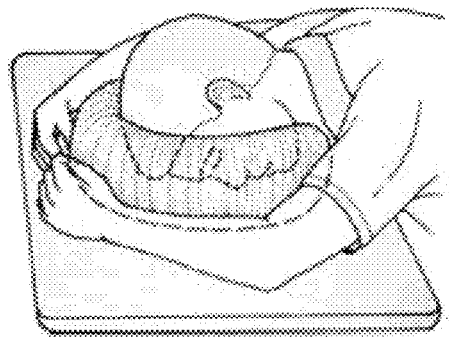
FIG. 14 This figure illustrates a side view of patient positioning, electrical polarity and position of unit one, placed on the scar, and unit two, placed on B62, during Fascia Release-SRT Method.
Figure 15:
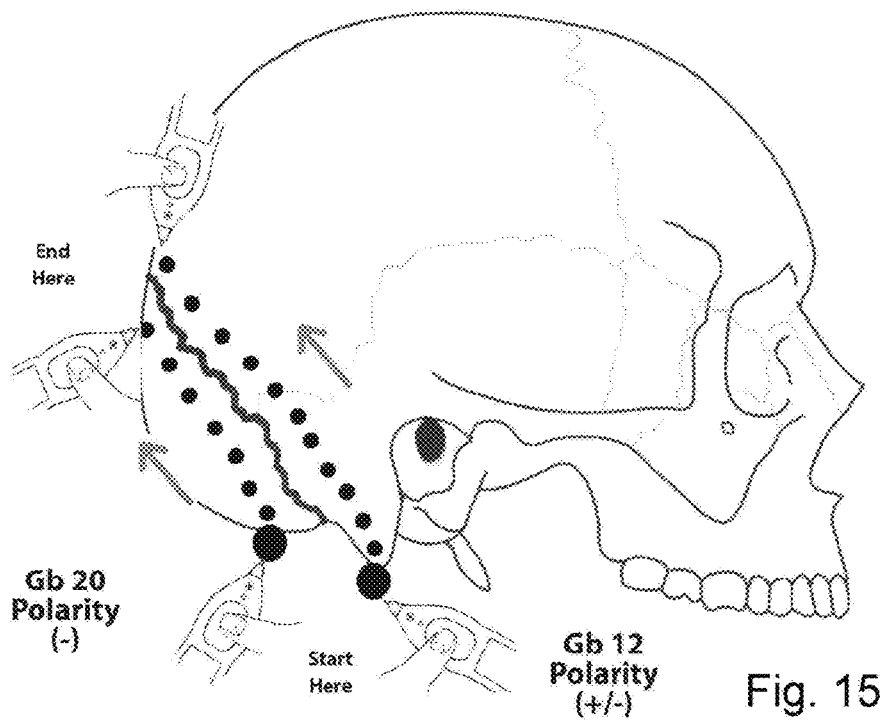
FIG. 15 This figure illustrates a view of acupuncture point St36 and the methodology placement and polarity settings of unit one and unit two during Adhesion Release-SRT Method.
Figure 16:
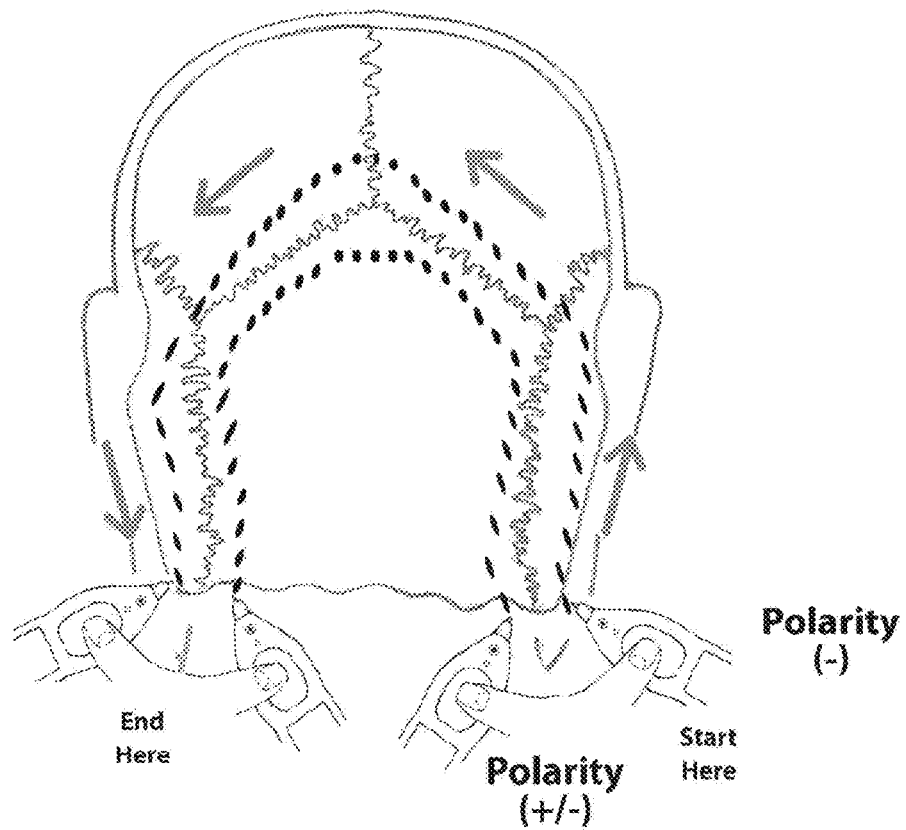
FIG. 16 Application methodology Occipitlomastoid-Lambdoid Suture release-MPS Method—Posterior View.
Figure 17:
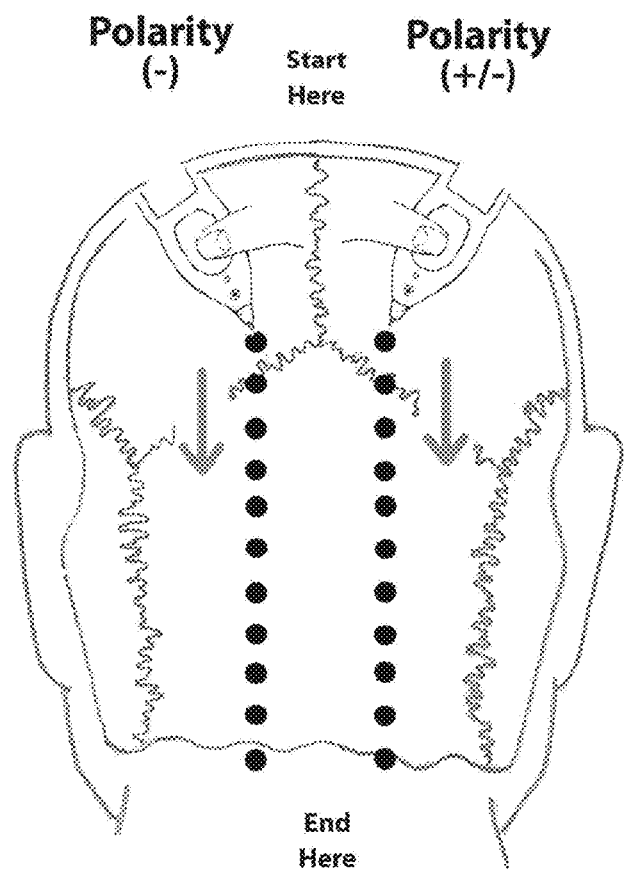
FIG. 17 Application methodology of Occipitlomidline Release-MPS Method—Posterior View.
Figure 18:
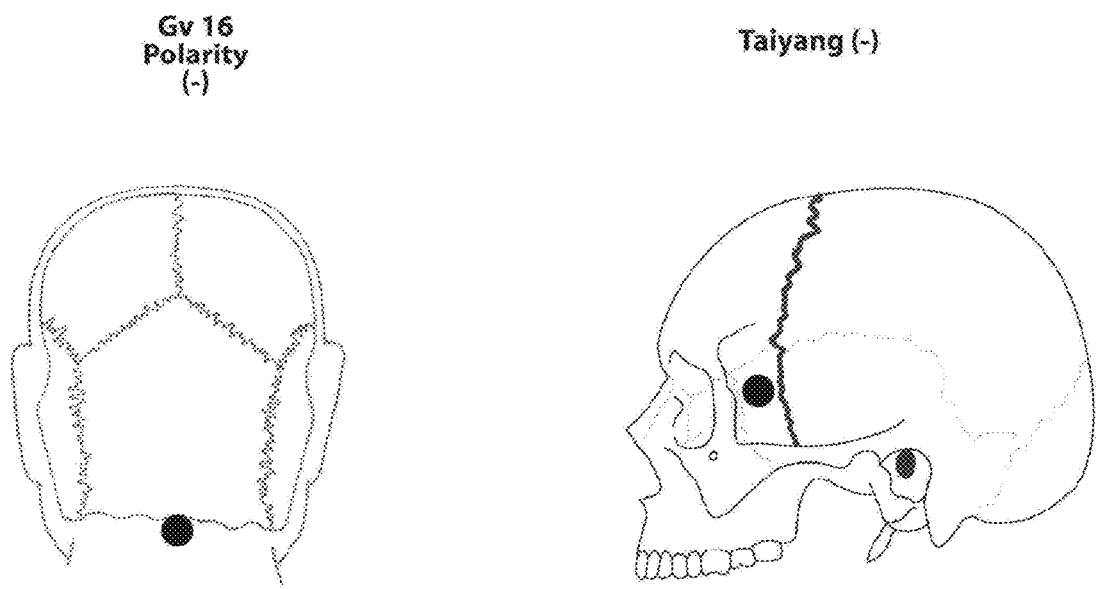
FIG. 18. Application methodology and electrical polarity Application methodology and polarity of Sphenoid-Balance-MPS Method Gv 16—Taiyang.
Figure 19:
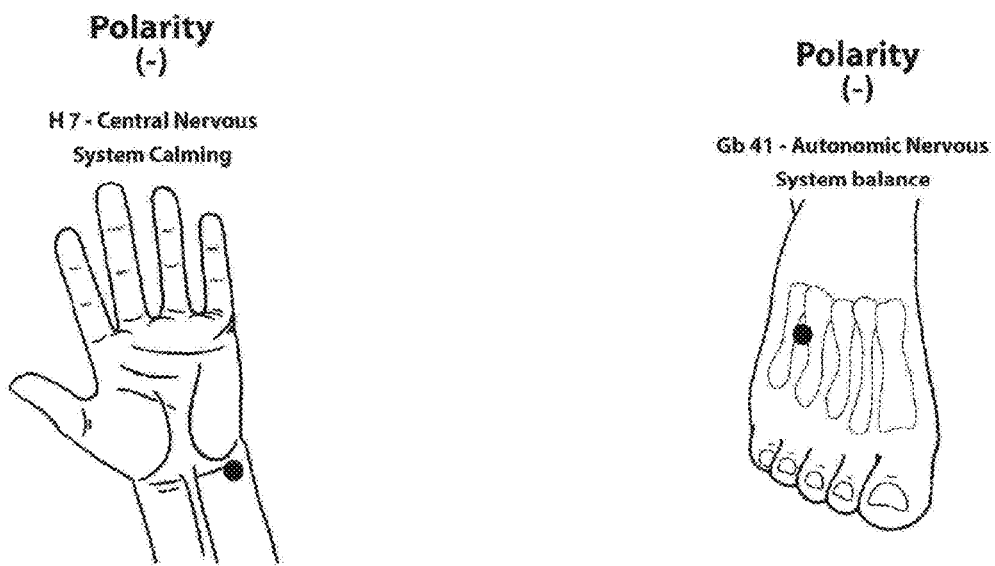
FIG. 19. Application methodology and electrical polarity of devices during Autonomic Nervous System balance-CRT MPS Method Gb 41-H7—Autonomic Nervous System Balance.
Figure 20:
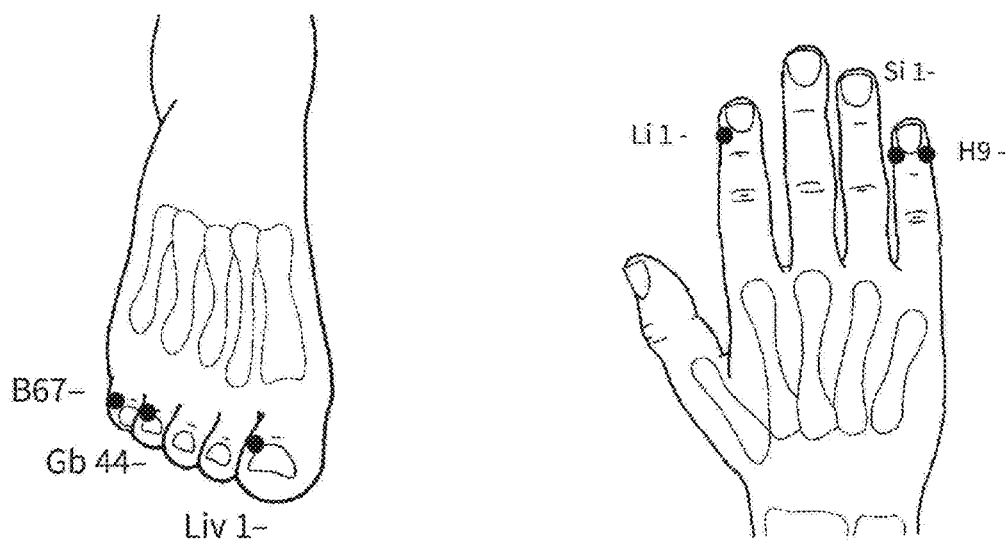
FIG. 20. Application methodology and electrical polarity of devices during increased brain vascularity-CRT MPS Method—Jing Points—B67, Gb 44, Liv 1. Li1, Si1, H9.
Figure 21:
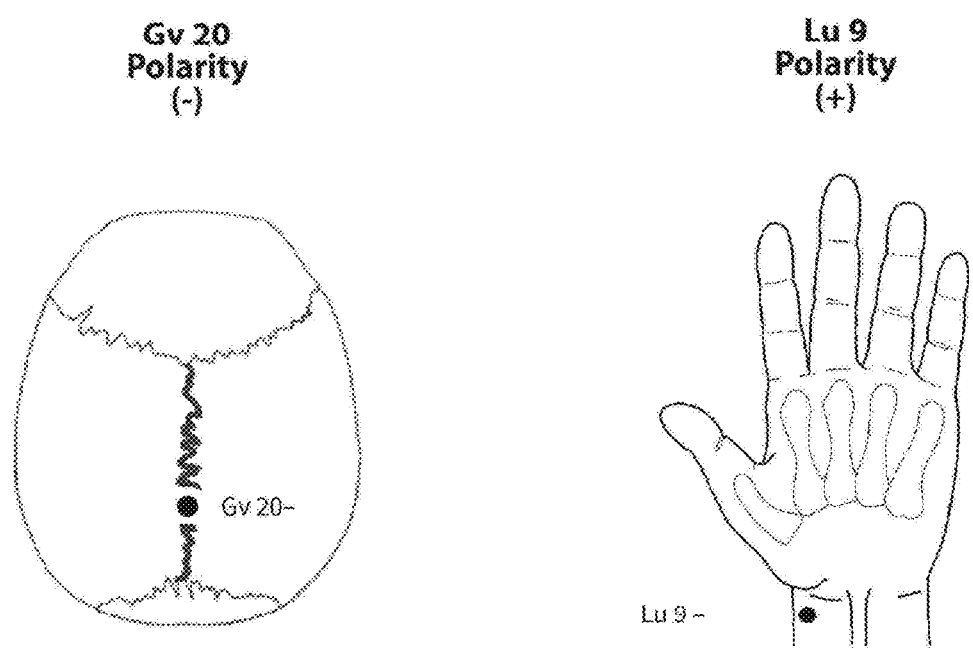
FIG. 21. Application methodology and electrical polarity of devices during increased brain vascularity-CRT MPS Method Gv 20-Lu 9.
Figure 23:
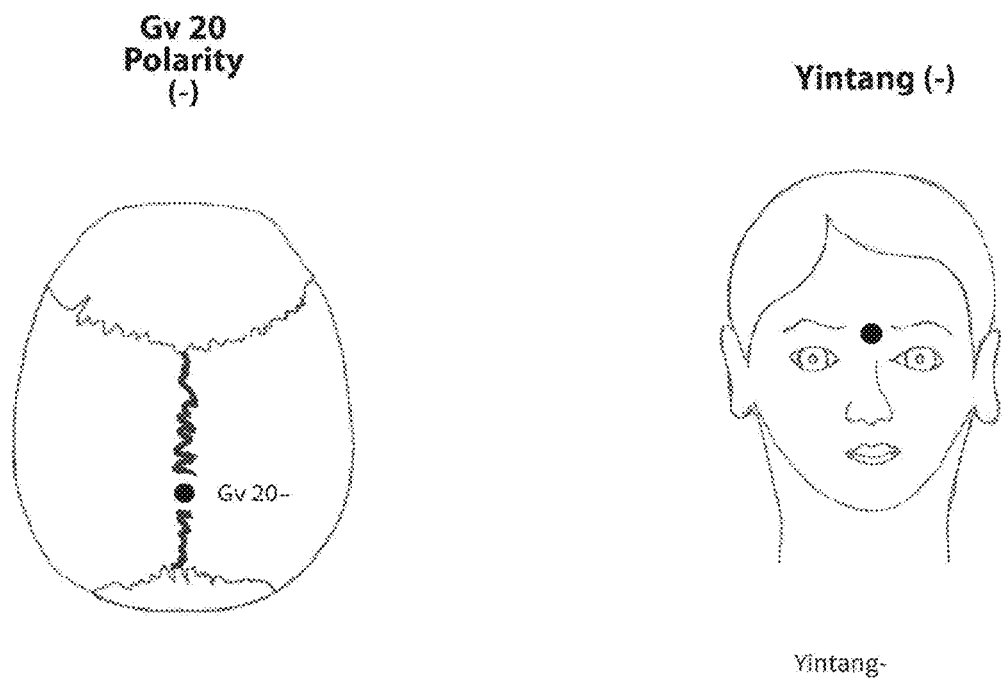
FIG. 23. Application methodology and electrical polarity of devices during Autonomic Nervous System Rebalance-CRT MPS Method Gv 20-Yintang.
Figure 24:
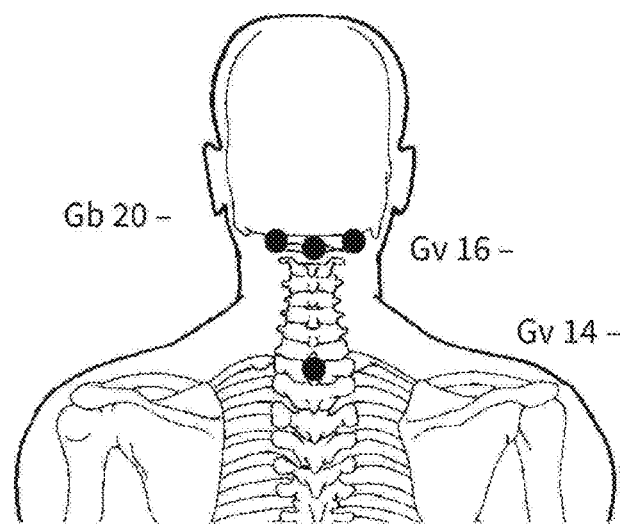
FIG. 24. Application methodology and electrical polarity of devices during Posterior Neck Release-CRT MPS Method—Gb 20, Gv 16 and Gv 14.
Figure 25:
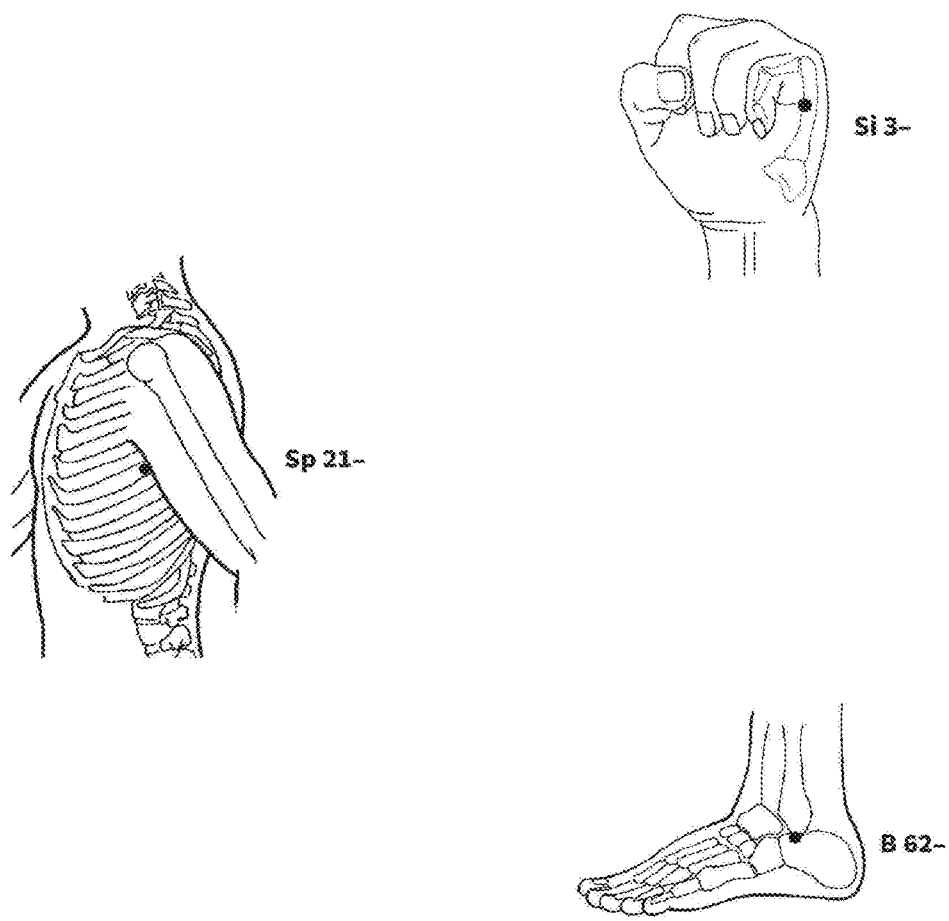
FIG. 25. Application methodology and electrical polarity of devices during Central-Peripheral Nervous System Reconnection-CRT MPS Method—Si3, B62, Sp 21.
Figure 26:
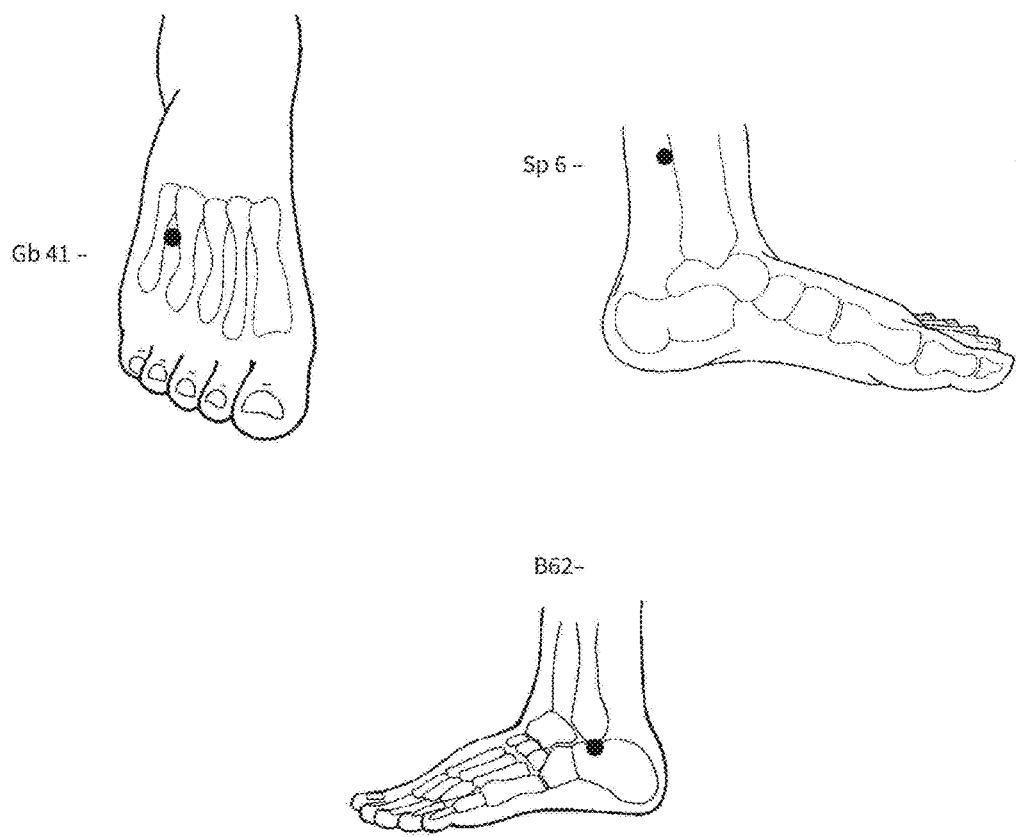
FIG. 26. Application methodology and electrical polarity of devices during Neuro-Vascular Reconnection-CRT MPS Method—Gb 41, Sp 6, B 62.

Several drawings and illustrations have been presented to aid in understanding the present invention. The scope of the present invention is not limited to what is shown in the figures.

DESCRIPTION OF THE PREFERRED EMBODIMENTS

The prior art device used with the present invention produces a monophasic DC square wave which can be modified for enhanced application in suture tissue release treatment. A stuck suture is electrically depolarized or positive poled, and forcing a negative poled current through the suture is imperative for suture release. Manual therapies cannot reverse this tissue polarity. However, forcing concentrated micro-current stimulation through the suture with a dual co-ordinated electrical approach is a highly effective methodology.

The present invention involves the simultaneous, targeted para-suture application of two prior art Dolphin Neurostims™ devices at the approximate location and intervals as surgical stitching. On one side of the suture, the first hand-held device is pre-programmed to a negative polarity setting. Mirrored on the other side of the suture, the second opposing hand-held device is pre-programmed to the bipolar (+/−) or balancing setting.

The technique of the simultaneous cathode (−ve) and pulsed cathode/anode (+/−) micro-current application forces (pushes) negative poled electrical current back and forth through the positively poled suture tissue similar to surgical stitching. The entire length of the suture, along with both ends are treated with this sequential approach. This technique is repeated throughout the entire length of suture with the placement of the hand-held devices during application being mirrored opposite to each other on the suture to optimize (maximize) tissue change.

The true embodiment of this present invention is the unique application process, which integrates the unique dual application of concentrated micro-current applied to each side of sutures along its entire length, and then the integration of the locked sutures with key acupuncture points that have the intent of enhancing electrical re-connections, vascularity to brain and balance within the nervous systems.

An important part of the present invention is the application process which integrates the dual application of micro-current applied to each side of sutures along their entire length, and then the integration of the locked sutures with key acupuncture points that have the intent of enhancing electrical re-connections, vascularity to brain and balance within the nervous systems.

After the treatment, there are no physical limitations imposed allowing the patient to immediately resume normal daily activities. The treatment technique is simple to learn and may be easily and safely applied to others with a minimal amount of training. During application, patients report a slight tingling sensation followed by an overall feeling of relaxation and wellness.

The technique can be applied with a patient prone or supine with two Dolphin Neurostim units being simultaneously engaged around the perimeter of the suture. The engagement (treatment) requires the applicator (therapist) to locate Therapeutically Active Points (TAP's) (skin areas with lowered electrical resistance) beside the sutures and then initiate the activation phase which forces (pushes) the negatively poled current through the positively poled injured suture tissue. During activation phase, patients perceive a slight tingling sensation which is not uncomfortable or irritating. The application of technique may be integrated with other therapies and will not interfere or produce adverse (iatrogenic) responses with any known prescribed medicine.

CRT-MPS Method Application Methodology

Summary: this present invention provides a methodology for effectively treating cranial sutures for health related benefits. The outcomes produced using the unique application methodology of bi-lateral, negative poled, (focused) concentrated micro-current stimulation, at a cellular influencing low frequency & low amplitudes what makes this application worthy. Applying this stimulation in the following sequential manner can often produce significant sympathetic deregulation and visible and cognitive changes within one application.

Sagittal Suture Release

Step 1: Patient may either be in prone or supine position. Start at the at the tips of the eyebrows, and place one DOLPHIN NEUROSTIM (unit one) at the inner tip of the eyebrow, ½ inch to one side of midline (the devices will register the low resistance and precisely identify this location). Place other DOLPHIN NEUROSTIM (unit two) at the inner tip of the other opposite eyebrow, ½ inch to one side of midline. Unit one has a pre-selected negative (−ve) polarity, and Unit two is preset to positive/negative polarity (+/−). Which side on suture has (−ve) or (+/−ve) does not matter, only polarity of stimulation and methodology matters. Both units are then simultaneously activated and held in place for 30 seconds. The two DOLPHIN NEUROSTIM devices are then moved ¼" down the suture, held in place and then reactivated for another 30 second time frame. This process is repeated every ¼ inch along the entire length of the midline and throughout the sagittal suture until applicator reaches the Lambdoid suture at the crown of the head. The primary goal of this step is to provide sympathetic deregulation and balance of the autonomic nervous system.

Step 2: With patient still in prone or supine position, place unit one on acupuncture point GV 20 and unit 2 on H7 and electrically connect for enhanced sympathetic deregulation and balance of the autonomic nervous system. Repeat H7 both wrists, keeping GV 20 static. Both units one and two are preset to negative poled currents during this step.

Sphenosquamosal-Cornonal Suture Release

Step 3: Patient may either be in prone or supine position, but head must be tilted to one side. Identify Temporomandibular joint (jaw) in front of ear. Place Unit one two fingers above temporomandibular joint on top of zygomatic arch. Place Unit two in the anterior angle of zygomatic arch, approximately one half inch in front of Sphenosquamosal suture and one inch in front of unit one. Unit one has a pre-selected negative (−ve) polarity, and Unit two is preset to positive/negative polarity (+/−). Both units are then simultaneously activated and held in place for 30 seconds. The two DOLPHIN NEUROSTIM devices are then moved ¼" up the suture towards the midline held in place and then reactivated for another 30 second time frame. This process is repeated towards midline over Sphenosquamosal suture, the sphenofrontal suture, and finally the coronal suture, ending at the brema (meeting of coronal and sagittal sutures). Devices are kept one inch apart during each treatment phase, and application is repeated every ¼ inch along the entire length of the suture chain.

Step 4: With patient in supine position, connect acupuncture point taiyang (anterior tempro bone) with Gb 27 (anterior tip of iliac crest) for enhanced release and balance of the sphenoid bone and relating hip bones. If prone, connect acupuncture point Gb 3 (posterior tempro bone) with Gb 30 (piriformis) for similar enhanced release and balance of the sphenoid bone and hips. Both units are preset to negative poled currents and points are electrically connected in a contra laterally (opposite) methodology.

Step 5: Repeat same sequential treatment process as in step 3 and 4 (Sphenosquamosal-Cornonal Suture Release and balance) for opposite side of head.

Spenofrontal/Squamosal Suture Release

Step 6: Patient may either be in prone or supine position, but head must be tilted to one side. Start at the end of the eyebrow. Place Unit one in the anterior angle of zygomatic arch. Unit two is placed ¼ inch above outer end of eyebrow, approximately one inch above unit one. In this position, units one and two now bridge the frontozygomatic suture. On one side the DOLPHIN NEUROSTIM is has a pre-selected negative (−ve) polarity, and on the other a positive/negative polarity (+/−). Which side has (−ve) or (+/−ve) does not matter, only polarity of stimulation matters. Both units are then simultaneously activated and held in place for 30 seconds. Both units are then moved backward ¼ inch over frontosphenoid suture, held in place and then reactivated for another 30 second time frame. This process is repeated every ¼ inch along length of entire squamosal suture towards the back of head, with both units ending at acupuncture point Gb 12 (behind and under the mastoid process) and acupuncture point GB 20 (below the occiput) and covers the frontosphenoid, squamous, parietomastoid and occiptomastoid sutures.

Step 7: With patient in supine position, connect acupuncture point connect acupuncture point Gb 20 (below occipital bone) with Yintang (between eyebrows) for balance of the sphenoid bone and sympathetic deregulation through reduction of vagal tone. Both units are preset to negative poled currents.

Step 8: Repeat same sequential treatment process as in step 6 and 7 (Spenofrontal/Squamosal Suture Release and balance) for opposite side of head.

Occiptomastoid/Lambdoid Suture Release

Step 9: Patient must be in prone position, with head tilted slightly to one side. Start at the ending point of step 3, unit one placed at acupuncture Gb 12 and unit two placed on acupuncture point GB 20. The two DOLPHIN NEUROSTIM devices now bridge the inferior end of the occiptomastoid suture, approximately one inch apart. Unit one has a pre-selected negative (−ve) polarity, and unit two is preset to positive/negative polarity (+/−). Which side has (−ve) or (+/−ve) does not matter, only polarity of stimulation matters. Both units are then simultaneously activated and held in place for 30 seconds. The two devices are then simultaneously moved ¼ inch upwards towards crown midline over occiptomastoid, held in place and then reactivated for another 30 second time frame. This process is repeated every ¼ inch along the occiptomastoid and Lambdoid sutures ending at the sagittal suture (midline). Repeat and apply to both sides.

Step 10: With patient in prone position, connect acupuncture point connect acupuncture point Gv 16 (occiput) with acupuncture point taiyang (anterior tempro bone) for balance of the sphenoid bone and sympathetic deregulation. Both units are preset to negative poled currents.

Step 11: Repeat same sequential treatment process as in step 9 and 10 (Lambdoid/Occiptomastoid Suture Release and sphenoid balance) for opposite side of head.

Occiptomidline Release

Step 12: Patient in prone position. Start at the midline, where the Lambdoid/sagittal sutures meet. Place two DOLPHIN NEUROSTIM ½ inch to each side of midline (the devices will register the low resistance tissue and identify this location). On one side the DOLPHIN NEUROSTIM is has a pre-selected negative (−ve) polarity, and on the other a positive/negative polarity (+/−). Which side on suture has (−ve) or (+/−ve) does not matter, only polarity of stimulation matters. Both units are then simultaneously activated and held in place for 30 seconds. The two DOLPHIN NEUROSTIM devices are then moved ¼" down beside the midline towards neck, held in place and then reactivated for another 30 second time frame. This process is repeated every ¼ inch along the entire length starting at the sagittal suture and ending at the inferior angle of the occipital protuberance, ½ inch to each side of acupuncture point Gv 16.

Step 13: With patient in prone position, connect acupuncture point connect acupuncture point Gv 16 (occiput) with B 31 (2nd sacral foremen at Sacro-iliac joint) for final balance of the autonomic nervous system, occiput and sacrum bones and reduction of spinal torsion. Both units are preset to negative poled currents while Gv 16 is static and both B31 points are treated. Repeat application on both sides.

Additional CRT-MPS Application Methodology for Traumatic Brain Injuries

Step 14: To balance the autonomic nervous system after such a sympathetic release, the following two acupuncture points have been discovered to highly effective when treated with microcurrent. Gb 41 and H 7. Both are treated on negative (−ve) polarity and are a critical step in ensuring a long term autonomic nervous system balance.

Step 15: The following acupuncture Jing points have been discovered to increase brain vascularity when treated with microcurrent. Jing Points H9, Li 1 and Si 1 in the hands, and B67, Gb 44 and Liv 1 in the feet, when treated on negative (−ve) polarity and are a critical step in expedited recovery from traumatic brain injuries.

Step 16: The following acupuncture points have been discovered to increase brain vascularity when treated with microcurrent. Gv 20 and Lu9. Place unit one on Gv 20 preset on negative polarity. Place unit two on Lu9 preset on positive polarity.

Step 17: To rebalance the sphenoid bone after traumatic brain injuries, the following three acupuncture points have been discovered to highly effective when treated with microcurrent. Gv 16 and Yintang and taiyang. All are treated preset on negative (−ve) polarity and are a critical step in ensuring successful traumatic brain injury and long term autonomic nervous system balance.

Step 18: To rebalance the autonomic nervous system, the following two acupuncture points have been discovered to highly effective when treated with microcurrent. Gv 20 and Yintang. Both are preset to negative (−ve) polarity and are critical in ensuring in expedited recovery from traumatic brain injuries.

Step 19: To reconnect the central nervous system (CNS) with the peripheral nervous system (PNS), the following three acupuncture points have been discovered to highly effective when treated with microcurrent. B62, Si 3 and Sp 21 are all treated preset on negative (−ve) polarity and are a critical step in expedited recovery from traumatic brain injuries.

Step 20: To treat and release the neck muscles, which are often compromised during traumatic brain injuries, the following three acupuncture points have been discovered to highly effective when treated with microcurrent. Gb 20, Gv 16, Gv 14. All are treated on negative (−ve) polarity and are a critical step in expedited recovery from traumatic brain injuries.

Step 21: To move stagnant circulation upwards to heal the brain, the following acupuncture points have been discovered to highly effective final step in vascular movement from the feet to the brain and balancing the autonomic nervous system when treated with microcurrent. Gb 41, B 62 and Sp 6. All are treated on negative (−ve) polarity and are a critical step in expedited recovery from traumatic brain injuries.

Several descriptions and illustrations have been presented to aid in understanding the present invention. One with skill in the art will realize that numerous changes and variations may be made without departing from the spirit of the invention. Each of these changes and variations is within the scope of the present invention.

I claim:

1. A method using two electronic microcurrent injection devices, each having and electrode tip, in a mirrored relationship to electrically treat cranial sutures by applying negative poled electrical microcurrent stimulation directly through sutures in order to promote increased metabolism, balance the autonomic nervous system and promote cellular homeostasis comprising the following steps performed in order:

(a) injecting a negative polarity DC electrical microcurrent by starting at a first eyebrow inner tip, placing the electrode tip of a first electronic microcurrent injection device ½ inch to side of midline, the first electronic microcurrent injection device injecting a negative polarity DC electrical microcurrent through its electrode tip;

(b) injecting a positive/negative polarity square wave electrical microcurrent by continuing at a second eyebrow inner tip, placing the electrode tip of a second electronic microcurrent injection device ½ inch to side of midline, the second electronic microcurrent injection device injecting a positive/negative polarity pulsed square wave electrical microcurrent through its tip; the first and second electronic microcurrent injection devices acting in a mirror relationship to one-another causing a negative poled electrical microcurrent to flow back and forth between the first and second electronic microcurrent injection device promoting cellular homeostasis;

(c) holding both the first and second electronic microcurrent injection devices in place for 30 seconds;

(d) moving both the first and second electronic microcurrent injection devices ¼" along the suture;

(e) repeating steps (c) and (d) until a Lambdoid suture is reached.

2. The method of claim 1 further comprising the following steps performed in order:

injecting a negative polarity DC electrical microcurrent by placing the first electronic microcurrent injection device on acupuncture point GV 20 and the second electronic microcurrent injection device on acupuncture point H7 on a first wrist for 30 seconds with the first and second electronic microcurrent injection device both set to inject a negative polarity DC electrical microcurrent, and then:

injecting a negative polarity DC electrical microcurrent by placing the second electronic microcurrent injection device on acupuncture point H7 on a second wrist for 30 seconds.

3. The method of claim 2 further comprising:

(f) injecting a negative polarity DC electrical microcurrent by placing the first electronic microcurrent injection device approximately 1 inch above temporomandibular joint on top of zygomatic arch with the first electronic microcurrent injection device set to inject a negative polarity DC electrical microcurrent;

(g) injecting a positive/negative polarity square wave electrical microcurrent by placing the second electronic microcurrent injection device in anterior angle of zygomatic arch approximately ½ inch in front of spenosquamosal suture with the second electronic microcurrent injection device set to inject positive/negative polarity square wave electrical microcurrent;

(h) holding both the first and second electronic microcurrent injection devices in place for 30 seconds;

(i) moving both electronic microcurrent injection devices ¼ inch up the suture;

(j) repeating steps (h) and (i) until the brema is encountered.

4. The method of claim 3 further comprising injecting a negative polarity DC electrical microcurrent by placing the first electronic microcurrent injection device on acupuncture point Gb 3 and the second electronic microcurrent injection device on acupuncture point Gb 30 for 30 seconds with the first and second electronic microcurrent injection devices set to inject a negative polarity DC electrical microcurrent.

5. The method of claim 4 further comprising the following additional steps performed in order:

(k) injecting a negative polarity DC electrical microcurrent by placing the first electronic microcurrent injection device in anterior angle of zygomatic arch approximately ½ inch in front of spenosquamosal suture with the first electronic microcurrent injection device set to inject a negative polarity DC electrical microcurrent;

(l) injecting a positive/negative polarity square wave electrical microcurrent by placing the second electronic microcurrent injection device approximately 1 inch above the first electronic microcurrent injection device so that the first and second units bridge frontozygomatic suture with the second electronic microcurrent injection device set to inject a positive/negative polarity square wave electrical microcurrent;

(m) holding both the first and second electronic microcurrent injection devices in place for 30 seconds;

(n) moving both electronic microcurrent injection devices ¼ inch up the suture;

(o) repeating steps (m) and (n) until acupuncture point Gb12 is encountered.

6. The method of claim 5 further comprising injecting a negative polarity DC electrical microcurrent by placing the first electronic microcurrent injection device on acupuncture point Gb 20 and the second electronic microcurrent injection device on acupuncture point yintang for 30 seconds with the first and second electronic microcurrent injection devices set to inject a negative polarity DC electrical microcurrent.

7. The method of claim 6 further comprising the following steps performed in order:

(p) injecting a negative polarity DC electrical microcurrent by placing the first electronic microcurrent injection device at acupuncture point Gb 12 with the first electronic microcurrent injection device set to inject a negative polarity DC electrical microcurrent;

(q) injecting a positive/negative polarity square wave electrical microcurrent by placing the second electronic microcurrent injection device at acupuncture point G20 with the second electronic microcurrent injection device set to inject a positive/negative polarity square wave electrical microcurrent;

(r) holding both the first and second electronic microcurrent injection devices in place for 30 seconds;

(s) moving both electronic microcurrent injection devices ¼ towards crown midline over occiptomastoid;

(t) repeating steps (r) and (s) until Sagittal suture is encountered.

8. The method of claim 7 further comprising placing the first electronic microcurrent injection device on acupuncture point Gv 16 and the second electronic microcurrent injection device on acupuncture point taiyang for 30 seconds with the first and second electronic microcurrent injection devices set to inject a negative polarity DC electrical microcurrent.

9. The method of claim 8 further comprising the following additional steps performed in order:

(u) injecting a negative polarity DC electrical microcurrent by placing the first electronic microcurrent injection device ½ inch off midline where Lambdoid/sagittal sutures meet with the first electronic microcurrent injection device set to inject a negative polarity DC electrical microcurrent;

(v) injecting a positive/negative polarity square wave electrical microcurrent by placing the second electronic microcurrent injection device ½ inch off midline in opposite direction where Lambdoid/sagittal sutures meet with the second electronic microcurrent injection device set to inject a positive/negative polarity square wave electrical microcurrent;
- (w) holding the first and second electronic microcurrent injection devices in place for 30 seconds;
- (x) moving both electronic microcurrent injection devices ¼ toward neck;
- (y) repeating steps (w) and (x) until acupuncture point Gv 16 is encountered.

10. The method of claim 9 further comprising:
- injecting a negative polarity DC electrical microcurrent by placing the first electronic microcurrent injection device on acupuncture point Gv 16 and the second electronic microcurrent injection device on acupuncture point B31 for 30 seconds with the first and second electronic microcurrent injection devices set to inject a negative polarity DC electrical microcurrent of;
- injecting a negative polarity DC electrical microcurrent by placing the first electronic microcurrent injection device on acupuncture point Gb 41 and the second electronic microcurrent injection device on acupuncture point H7 for 30 seconds with the first and second electronic microcurrent injection devices set to inject a negative polarity DC electrical microcurrent of;
- injecting a negative to positive to positive polarity DC electrical microcurrent by placing the first electronic microcurrent injection device on acupuncture point Gv 20 and the second electronic microcurrent injection device on acupuncture point Lu 9 for 30 seconds with the first electronic microcurrent injection device set to inject microcurrent of negative polarity and the second electronic microcurrent injection device set to inject a positive polarity DC electrical microcurrent;
- placing the first electronic microcurrent injection device on acupuncture point Gv 20 and the second electronic microcurrent injection device on acupuncture point yintang for 30 seconds with the first and second electronic microcurrent injection devices set to inject a negative polarity DC electrical microcurrent.

11. The method of claim 1 further comprising the following steps performed in order:
- (f) injecting a negative polarity DC electrical microcurrent by placing the first electronic microcurrent injection device approximately 1 inch above temporomandibular joint on top of zygomatic arch with the first electronic microcurrent injection device set to inject a negative polarity DC electrical microcurrent;
- (g) injecting a positive/negative polarity square wave electrical microcurrent by placing the second electronic microcurrent injection device in anterior angle of zygomatic arch approximately ½ inch in front of spenosquamosal suture with the second electronic microcurrent injection device set to inject positive/negative polarity square wave electrical microcurrent;
- (h) holding both the first and second electronic microcurrent injection device in place for 30 seconds;
- (i) moving both electronic microcurrent injection devices ¼ inch up the suture;
- (j) repeating steps (h) and (i) until the brema is encountered.

12. The method of claim 1 further comprising: injecting a negative polarity DC electrical microcurrent by placing the first electronic microcurrent injection device on acupuncture point Gb 3 and the second electronic microcurrent injection device on acupuncture point Gb 30 for 30 seconds with the first and second electronic microcurrent injection devices both set to inject a negative polarity DC electrical microcurrent.

13. The method of claim 1 further comprising:
- (k) injecting a negative polarity DC electrical microcurrent by placing the first electronic microcurrent injection device in anterior angle of zygomatic arch approximately ½ inch in front of spenosquamosal suture with the first electronic microcurrent injection device set to inject a negative polarity DC electrical microcurrent;
- (l) injecting a positive/negative polarity square wave electrical microcurrent by placing the second electronic microcurrent injection device approximately 1 inch above the first electronic microcurrent injection device so that the first and second electronic microcurrent injection devices bridge frontozygomatic suture with the second electronic microcurrent injection device positive/negative polarity square wave electrical microcurrent;
- (m) holding both the first and second electronic microcurrent devices in place for 30 seconds;
- (n) moving both the first and second electronic microcurrent devices ¼ inch up the suture;
- (o) repeating steps (m) and (n) until acupuncture point Gb12 is encountered.

14. The method of claim 1 further comprising injecting a negative polarity DC electrical microcurrent by placing the first electronic microcurrent injection device on acupuncture point Gb 20 and the second electronic microcurrent injection device on acupuncture point yintang for 30 seconds with the first and second electronic microcurrent injection devices set to inject a negative polarity DC electrical microcurrent.

15. The method of claim 1 further comprising performing the following additional steps in order:
- (p) injecting a negative polarity DC electrical microcurrent by placing the first electronic microcurrent injection device at acupuncture point Gb 12 with the first electronic microcurrent injection device set to inject a negative polarity DC electrical microcurrent;
- (q) injecting a positive/negative polarity square wave electrical microcurrent by placing the second electronic microcurrent injection device at acupuncture point Gv 20 with the second electronic microcurrent injection device set to inject a positive/negative polarity square wave electrical microcurrent;
- (r) holding the first and second electronic microcurrent injection devices in place for 30 seconds;
- (s) moving both the first and second electronic microcurrent injection devices ¼ towards crown midline over occiptomastoid;
- (t) repeating steps (r) and (s) until sagittal suture is encountered.

16. The method of claim 1 further comprising injecting a negative polarity DC electrical microcurrent by placing the first electronic microcurrent injection device on acupuncture point Gv 16 and injecting a negative polarity DC electrical microcurrent by placing the second electronic microcurrent injection device on acupuncture point taiyang for 30 seconds with the first and second electronic microcurrent injection devices set to inject a negative polarity DC electrical microcurrent.

17. The method of claim 1 further comprising the additional steps performed in order:
- (u) injecting a negative polarity DC electrical microcurrent by placing the first electronic microcurrent injection device ½ inch off midline where Lambdoid/sagittal sutures meet with the first device set to inject a negative polarity DC electrical microcurrent;
(v) injecting a positive/negative polarity square wave electrical microcurrent by placing the second electronic microcurrent injection device ½ inch off midline in opposite direction where Lambdoid/sagittal sutures meet with the second device set to inject a positive/negative polarity square wave electrical microcurrent;
(w) holding the first and second electronic microcurrent injection devices in place for 30 seconds;
(x) moving both the first and second electronic microcurrent injection devices ¼ toward neck;
(y) repeating steps (w) and (x) until acupuncture point Gv 16 is encountered.

18. The method of claim 1 further comprising:
injecting a negative polarity DC electrical microcurrent by placing the first electronic microcurrent injection device on acupuncture point Gv 16 and the second electronic microcurrent injection device on acupuncture point B31 for 30 seconds with the first and second electronic microcurrent injection devices set to inject a negative DC electronic microcurrent;
injecting a negative polarity DC electrical microcurrent by placing the first electronic microcurrent injection device on acupuncture point Gb 41 and the second electronic microcurrent injection device on acupuncture point H7 for 30 seconds with the first and second electronic microcurrent injection devices set to inject a negative polarity DC electrical microcurrent;
injecting a negative to positive polarity DC electrical microcurrent by placing the first device on acupuncture point Gv 20 and the second electronic microcurrent injection device on acupuncture point Lu 9 for 30 seconds with the first electronic microcurrent injection device set to inject a negative polarity DC electrical microcurrent and the second device set to inject a positive polarity DC electrical microcurrent;
injecting a negative polarity DC electrical microcurrent by placing the first device on acupuncture point Gv 20 and the second electronic microcurrent injection device on acupuncture point yintang for 30 seconds with the first and second electronic microcurrent injection devices set to inject a negative polarity DC electrical microcurrent.

19. A method using two electronic microcurrent injection devices, each having and electrode tip, in a mirrored relationship to electrically treat cranial sutures by applying negative poled electrical microcurrent stimulation directly through sutures in order to promote increased metabolism, balance the autonomic nervous system and promote cellular homeostasis comprising the following steps taken in order:
(a) injecting a negative polarity DC electrical microcurrent by starting at a first eyebrow inner tip, placing the electrode tip of a first electronic microcurrent injection device ½ inch to side of midline, the first electronic microcurrent injection device injecting a negative polarity DC electrical microcurrent through its electrode tip;
(b) injecting a positive/negative polarity square wave electrical microcurrent by continuing at a second eyebrow inner tip, placing the electrode tip of a second electronic microcurrent injection device ½ inch to side of midline, the second electronic microcurrent injection device injecting a positive/negative polarity pulsed square wave electrical microcurrent through its tip; the first and second electronic microcurrent injection devices acting in a mirror relationship to one-another causing a negative poled electrical microcurrent to flow back and forth between the first and second electronic microcurrent injection device promoting cellular homeostasis;
(c) holding both the first and second electronic microcurrent injection devices in place for 30 seconds;
(d) moving both the first and second electronic microcurrent injection devices ¼" along the suture;
(e) repeating steps (c) and (d) until a Lambdoid suture is reached;
then performing the following steps in order:
(f) injecting a negative polarity DC electrical microcurrent by placing the first electronic microcurrent injection device approximately 1 inch above temporomandibular joint on top of zygomatic arch with the first electronic microcurrent injection device set to inject microcurrent of negative polarity;
(g) injecting a positive/negative polarity square wave electrical microcurrent by placing the second electronic microcurrent injection device unit in anterior angle of zygomatic arch approximately ½ inch in front of spenosquamosal suture with the second electronic microcurrent injection device set to inject positive/negative polarity square wave electrical microcurrent;
(h) holding both the first and second electronic microcurrent injection device in place for 30 seconds;
(i) moving both the first and second electronic microcurrent injection devices ¼ inch up the suture;
(j) repeating steps (h) and (i) until the brema is encountered.

* * * * *